US 6,632,207 B2

(12) United States Patent
Rangel et al.

(10) Patent No.: US 6,632,207 B2
(45) Date of Patent: Oct. 14, 2003

(54) INTIMATE NAPKIN

(75) Inventors: Fabio Eduardo Franca Rangel, Sao Paulo (BR); Francisco Antonio Rimoli, Sao Paulo (BR); Joao Bosco Pereira, Estado de Sao Paulo (BR); Jose Francisco Cau, Estado de Sao Paulo (BR); Julio Malva Filho, Sao Paulo (BR)

(73) Assignee: Johnson & Johnson Industria e Comercio Ltda., Sao Paulo (BR)

( * ) Notice: Subject to any disclaimer, the term of this patent is extended or adjusted under 35 U.S.C. 154(b) by 0 days.

(21) Appl. No.: 09/873,535

(22) Filed: Jun. 4, 2001

(65) Prior Publication Data

US 2002/0029027 A1 Mar. 7, 2002

(30) Foreign Application Priority Data

Sep. 6, 2000 (BR) .......................... 10004042

(51) Int. Cl.$^7$ ................................ A61F 13/20
(52) U.S. Cl. ............ 604/385.03; 604/358; 604/385.01; 604/385.04; 604/385.14; 604/386; 604/387
(58) Field of Search ............... 604/385.03, 356, 604/358, 365, 366, 367, 368, 375, 378, 385.01, 385.04, 385.05, 385.14, 386, 387, 389

(56) References Cited

U.S. PATENT DOCUMENTS

| | | | | |
|---|---|---|---|---|
| 3,913,580 A | * | 10/1975 | Ginocchio | 604/387 |
| 4,337,772 A | * | 7/1982 | Roeder | 604/385.03 |
| 4,605,403 A | * | 8/1986 | Tucker | 604/385.13 |
| 4,772,282 A | * | 9/1988 | Oakley | 604/385.03 |
| 5,135,521 A | * | 8/1992 | Luceri et al. | 604/383 |
| 5,275,591 A | * | 1/1994 | Mavinkurve | 604/378 |
| 5,354,400 A | * | 10/1994 | Lavash et al. | 156/196 |
| 5,415,650 A | * | 5/1995 | Sigl | 604/385.03 |
| 5,618,283 A | * | 4/1997 | Yamamoto | 604/387 |
| 5,670,004 A | * | 9/1997 | Mattingly, III | 156/227 |
| 5,694,739 A | * | 12/1997 | Mattingly, III | 53/429 |
| 5,849,003 A | * | 12/1998 | Olsen et al. | 604/385.03 |
| 2001/0020157 A1 | * | 9/2001 | Mizutani et al. | 604/385.04 |

FOREIGN PATENT DOCUMENTS

| | | | |
|---|---|---|---|
| DE | 33 44 593 C1 | 4/1985 | |
| DE | 298 23 625 U1 | 3/2000 | |
| EP | 0 270 058 A1 | 6/1988 | |
| EP | 689821 A2 | * 1/1996 | .......... A61F/13/56 |
| GB | 2273279 A | * 6/1994 | .......... B65D/85/16 |
| WO | WO 92/04000 A1 | 3/1992 | |

* cited by examiner

*Primary Examiner*—Henry Bennett
*Assistant Examiner*—Kathryn Ferko (57) ABSTRACT

An intimate napkin for use with an undergarment, having:

a substantially planar and elongated frame (3, 3') comprising a first face having a liquid pervious material layer, and a second face, opposite to the first face, having a liquid impervious material layer;

an absorbing core (2) inserted in the frame (3,3') between the liquid pervious material layer and the liquid impervious material layer, the liquid impervious material layer having a first inner surface faced to the core (2), and a second outer surface, opposite to the first surface, faced outwardly, which constitutes the outer face of the napkin (1,1'); and an adhesive layer applied to the second outer surface, the napkin (1,1'), wherein the adhesive layer is comprised of at least five lines of adhesive (4) substantially spaced apart, the adhesive ratio ranges from 8 to 25 g/m$^2$, and the adhesive has a shear value of at least 2.0 Kgf is disclosed.

26 Claims, 6 Drawing Sheets

CHART 1

FIG. 6

CHART 2

FIG. 7

CHART 3

FIG. 8

CHART 4

FIG. 11
CHART 7

INTIMATE NAPKIN

FIELD OF THE INVENTION

The present invention is directed to an intimate napkin provided with an adhesion member to be attached to the intimate undergarment, which member is comprised of adhesive lines.

DESCRIPTION OF THE STATE OF THE ART

Usually, intimate napkins are provided with only one adhesive strap to attach the intimate napkin to the panties or any other undergarment. The adhesive has a considerable area in relation to the size of the napkin.

However, this arrangement presents several shortcomings, such as those listed below.

First of all, the single adhesive strip causes the napkin to behave like a rigid body when attached to the panties, preventing same to move. Since there is only one adhesive strip, it is impossible to move only certain regions of the napkin, and a trend of shearing efforts of the napkin in relation to the panties, known as "shear", causes the napkin to be fully detached from the panties.

Secondly, the process for applying the adhesive element having a single strip is complicated and requires constant adjustments to the applying machine so that a satisfactory operation can be obtained. Nevertheless, failures are frequent in this process, due to the formation of certain regions where the adhesive is not applied. Despite the fact that most of the time such regions do not prevent the correct attachment of the napkin to the panties, the result is a sense of lack of quality, which might discourage the use of the product.

Thirdly, the displacement of the adhesive in relation to the napkin might occur due to failures when the same is applied. The displacement forms bubbles at the time the adhesive protecting film is removed, seriously jeopardizing the ability of the napkin to adhere to the panties and thus the efficiency thereof.

A known technique which is relevant to the present invention is described in document WO00/37015, which discloses an absorbent product, such as an intimate napkin, comprising a protecting film of the product adhesive strap adhered through a pressure sensitive adhesive to the outer end of the product. In order to enable the easy removal of the protecting film and keep suitable levels of the product fixation to the user's undergarment, the strength between the protecting film and the outer end of the product ("peel") should range between 0.5 and 1 Newton.

OBJECT OF THE INVENTION

The object of the present invention is to provide an intimate napkin having a multiplicity of thin adhesive lines, thus allowing a greater movement of the napkin when in use, however preventing the same from being detached from the user's panties, presenting a more aesthetically elaborated appearance and thus providing a greater reliability in the productive process thereof.

BRIEF DESCRIPTION OF THE INVENTION

The objects above are attained by an intimate napkin for use with an undergarment, comprising:

a substantially planar and elongated frame comprising a first face having a liquid pervious material layer, and a second face, opposite to the first face, having a liquid impervious material layer;

an absorbing core inserted in the frame between the liquid pervious material layer and the liquid impervious material layer, the liquid impervious material layer comprising a first inner surface faced to the core, and a second outer surface, opposite to the first surface, faced outwardly, which constitutes the outer face of the napkin; and an adhesive layer applied to the second outer surface, the adhesive layer being comprised of at least five lines of adhesive substantially spaced apart which the adhesive ratio ranges from 8 to 25 $g/m^2$, and the adhesive layer has a shear value of at least 2.0 Kgf.

Usually, the napkin comprises a layer of liquid pervious material or top sheet, which is fluid permeable and the function of which is to allow the passage of the menstrual fluid toward the absorbent core and thus to keep the fluid away from the user's body. It can be constituted of a non-woven layer or perforated plastic film or any material that may perform this function.

Usually, the napkin is also comprised of an outer layer of liquid impervious material or lining sheet, which is impervious or resistant to the passage of liquids and used to prevent the fluid absorbed by the absorbent core from leaking. It may be comprised of a non-perforated plastic sheet or any other material having such features. The lining sheet may also comprise a liquid pervious material such as a non-woven and other material that might play this role known by those skilled in the art.

The absorbent core is formed of cellulosic or textile synthetic fibers, such as rayon, polyester and the like. Its purpose is to contain the vaginal exudates. In the assumption the absorbent core contains superabsorbent material, said material can have a broad range of particle sizes and be distributed in a number of manners, for example, as a layer, film, or individual particles. As an example of superabsorbent material, sodium polymethacrilate or any other suitable superabsorbent material can be utilized.

The adhesive layer comprises at least five lines of adhesive substantially spaced apart.

Optionally, the napkin comprises two tabs projected substantially outwardly from two main ridges of the frame, and it may have the attaching adhesive formed by adhesive lines.

The napkin object of the present invention can undergo shearing efforts without being detached from the user's panties, does not require much adhesive without having a corresponding reduction in the attachment ability, is easy to apply through several lines, its manufacturing procedure is significantly easier and reliable than in the case where a single wide adhesive line is applied, and presents an aesthetic effect that pleases the user, thus encouraging the purchase of the napkin.

BRIEF DESCRIPTION OF THE DRAWINGS

The present invention will be described below in more details based on an example of execution shown in the drawings. The figures depict.

DETAILED DESCRIPTION OF THE DRAWINGS

Figure 1:
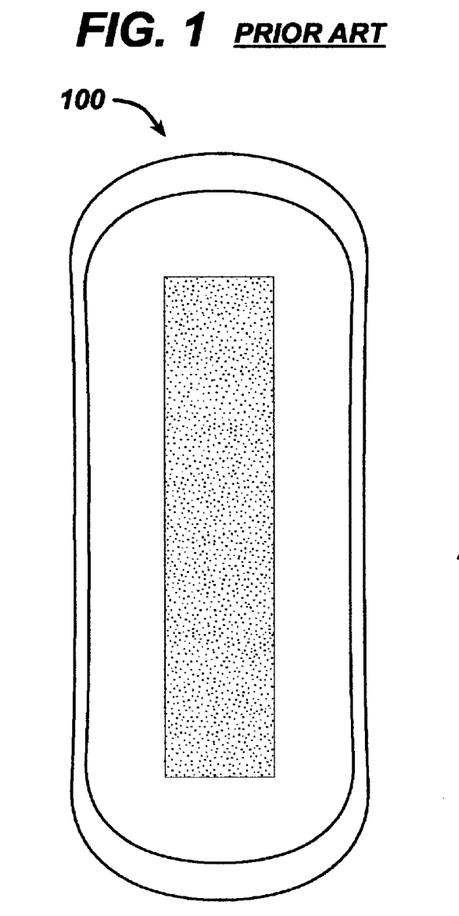
FIG. 1—a top view of a first variation of the intimate napkin of the state of the art.
Figure 2:
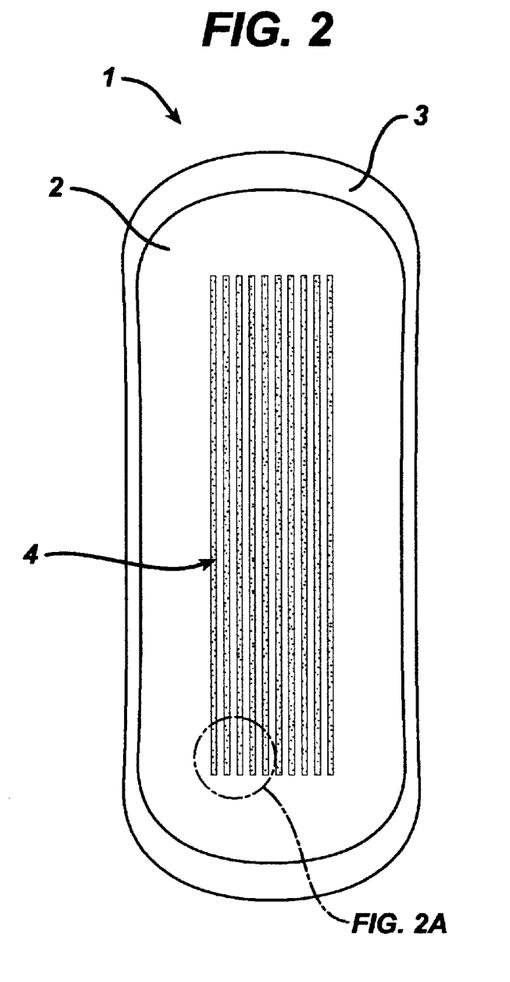
FIG. 2—a top view of a first variation of the intimate napkin object of the present invention.
Figure 2A:
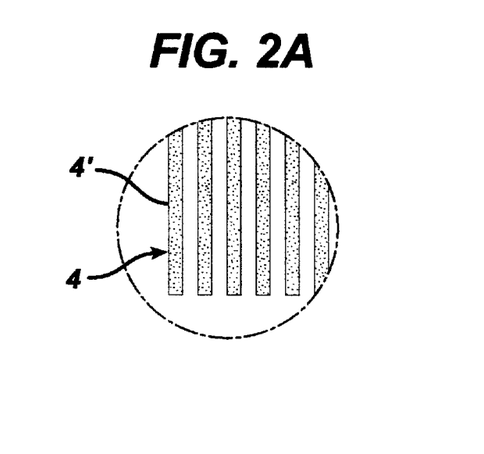

As can be seen in FIG. 2, a first variation of the intimate napkin 1 object of the present invention comprises a substantially planar and elongated frame 3, with its two main ridges presenting a substantially rectilinear shape and substantially parallel, and with its two secondary ridges presenting a substantially circular shape, thus forming semi-circumferences and having a radius substantially equal to half of the width of said frame 3. The central point of the semi-circumferences delimited by the secondary ridges is located substantially on the plane defined by the frame 3.

Figures 3, 4, 4A:
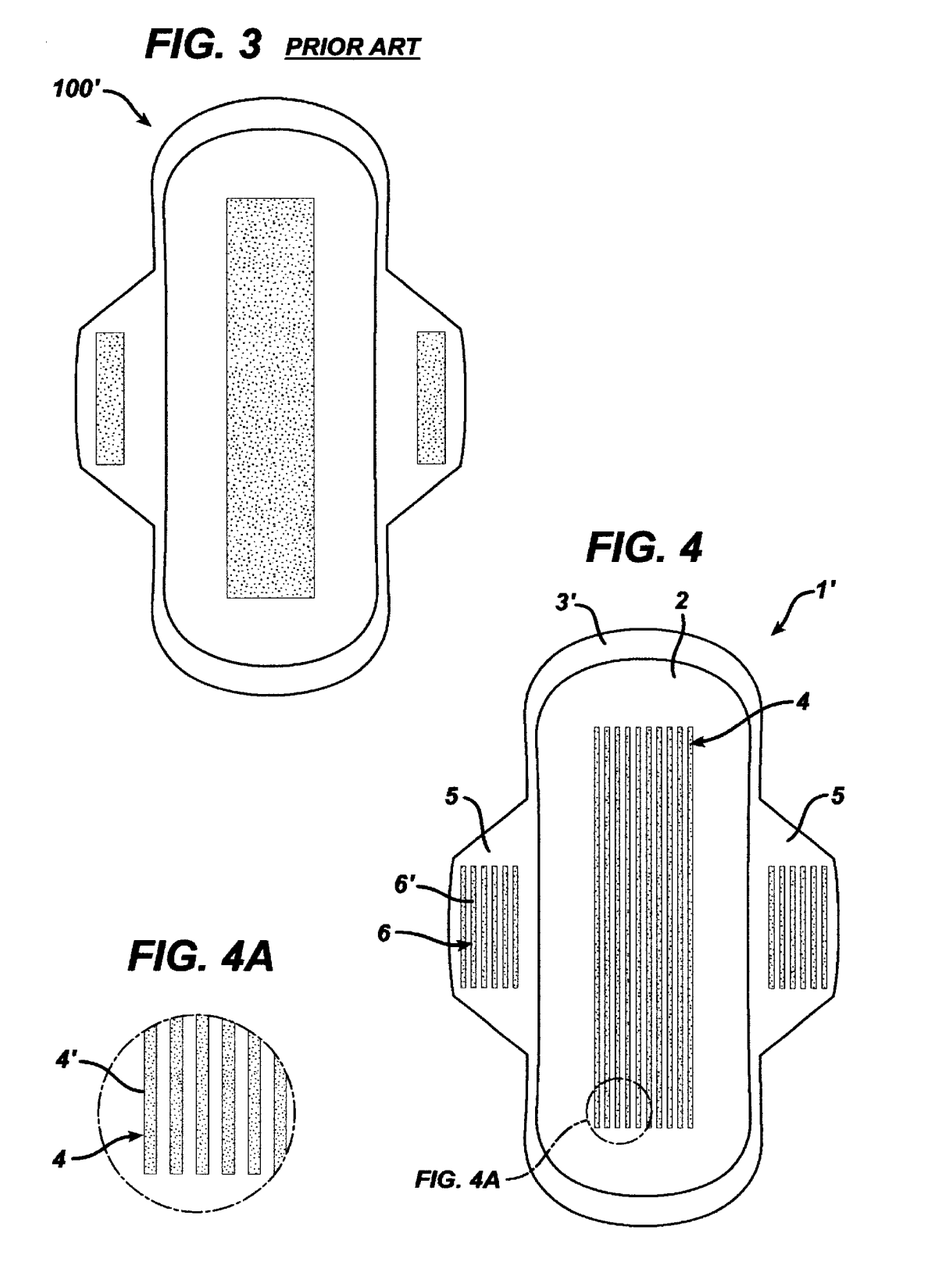
FIG. 3—a top view of a second variation of the intimate napkin of the state of the art.
FIG. 4—a top view of a second variation of the intimate napkin object of the present invention.

Referring to FIG. 4 a second variation of the intimate napkin 1 object of the present invention also presents a substantially planar and elongated frame 3' having secondary ridges virtually identical to those described in the preceding paragraph. However, the main ridges of the frame 3' present a substantially mid portion having a substantially trapezoidal shape substantially projecting outwards in relation to the ridges, thus forming two additional surfaces 5, also called tabs 5.

Both the frames 3, 3' comprise a first face having a liquid pervious material layer or top sheet of the napkin 1,1', which contacts the user's vaginal cavity, an absorbent core 2 which covers a substantial area of the frame 3,3', in such a manner to ease the correct absorption of the menstrual flow or menstruation, and a second face, opposite to the first face, having a liquid impervious material layer, or lining sheet, such as a plastic film, for instance. The absorbent core 2 is inserted between the said liquid pervious material layer and the liquid impervious material layer. The liquid impervious material layer or lining sheet comprises a first inner surface, faced to the core 2, and a second outer surface, opposite to said first surface, faced outwardly, which constitutes the outer face of the napkin 1,1' and contacts the undergarment's user when the napkin 1,1 ' has been in use.

In the embodiments shown in FIGS. 2 and 4, to the second outer surface of the liquid impervious material layer is applied an adhesive layer formed by a plurality lines of adhesive comprising the adhesive lines 4 applied substantially parallel to one another, defining therebetween regions 4' that are substantially free of adhesive. The number of adhesive lines 4, in turn, can range between five and twenty-five, more preferably ranging between eight and twenty and most preferably twelve. Thus, there is a region 4' that is intermediate adjacent lines of adhesive, the region 4' being substantially free of adhesive, said adhesive lines 4 and region 4' having a direction substantially coincident with the direction of the longitudinal length of the napkin 1,1', wherein the line 4 has a width, which ranges from 0.5 millimeters to 2.0 millimeters, more preferably from 1.0 millimeters to 1.8 millimeters and most preferably 1.2 millimeters and the region 4' has a width which ranges from 0.8 millimeters to 2.5 millimeters, more preferably from 1.0 millimeters to 1.8 millimeters and most preferably 1.2 millimeters.

The napkin 1' is also comprised of two adhesive layers located in a substantially central portion of the tabs 5, each of the adhesive layers of the tabs preferably having six adhesive lines which comprise an outer surface which contains the adhesive lines 6 applied substantially parallel to one another, defining therebetween regions that are substantially free of adhesive, the adhesive lines 6 and the regions 6' having a direction substantially coincident with the direction of the longitudinal length of the napkin 1', wherein the line 6 has a width from 0.5 millimeters to 1.5 millimeters, more preferably from 0.8 millimeters to 1.2 millimeters and most preferably 1.0 millimeters and the region 6' has a width from 0.8 millimeters to 2.0 millimeters, more preferably from 1.0 millimeters to 1.8 millimeters and most preferably 1.2 millimeters.

In order to preserve the adhering power of the napkin 1,1', before the same is utilized, a film of a substantially lightly adherent material (not shown), which can be easily removed without causing damage to the adhesive lines 4,6 is provided.

The twelve adhesive lines 4, alternated with the regions 4', cause the napkin 1,1' to undergo shearing efforts without being detached therefrom, since regions 4' function as deformable regions between the adhesive lines 4, allowing a deformation of certain regions of the napkin 1,1' without weakening same and, therefore, a decrease in the efficacy of the adhesive or even the partial and complete detachment from the panties.

The attachment adhesive utilized in the adhesive lines 4,6 can be mechanical (hook-loop type) or chemical, such as adhesives. The term adhesive means either double face adhesive ribbons, surfaces of a tacky texture, or any treatment on the lining sheet, the effect of which is to increase its adherence to a surface, layer or region. Such adhesives can be cold pressure sensitive, such as acrylate adhesives, generally combined with polyterpenes, block copolymers A-B-A or the like, such as the block copolymer styrene-butylene-styrene-styrene, for example, Stereon, or a two-block butadiene styrene AB adhesive, hot melt adhesives such as HM-6513 or HL 1972 from H. B. Fuller (St. Paul, Minn.) or N.S. 34-5509 from National Starch (Bridgewater, N.J.) are examples. Evidently, other adhesives different from the hot melt adhesive can also be used and shall be chosen based on several factors such as the adhesive compatibility with the other materials being used and with the final use of the absorbent product, and antioxidants and dyes can be included.

Preferably, the adhesive utilized in the adhesive lines 4,6 is of the hotmelt type, with a ratio between 8 $g/m^2$ and 25 $g/m^2$. The number of adhesive lines 4, in turn, can range between five and twenty-five, more preferably ranging between eight and twenty, while the number of adhesive lines 6 in the tabs 5 is at least two.

As mentioned above, the napkin 1,1' object of the present invention can undergo shearing efforts, known as "Shear", without being detached from the user's panties. Like other additional advantages, it requires less adhesive without having a corresponding reduction in the attachment ability, is easy to apply through several lines, its manufacturing procedure is significantly easier and more reliable than in the case when a single wide adhesive line is applied, and shows an aesthetic effect that pleases the user, encouraging the purchase of the napkin 1,1'.

The values mentioned above were obtained from the study of "Shear" in terms of the standard of the adhesive application intimate napkins—Response Surface Methodology (RSM) described as follows: "Shear" Results:

Referring to FIGS. 5–11, the results of the shearing efforts or "Shear" can be interpreted based on charts from 1 to 7, corresponding respectively to FIGS. 5 to 11, and they indicate an satisfactory adjustment of the data observed to a second grade polynomial function proposed in the central range of the studied interval of 3.0 to 3.5 as we can see in chart 1, which represents the observed value (Y) versus the value predicted by the model (Previewed Y).

Figure 5:
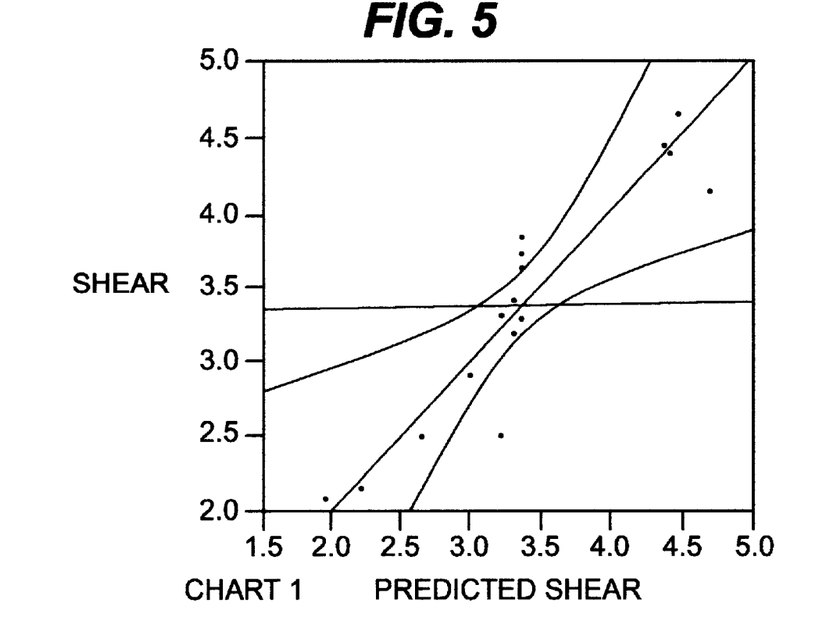
FIG. 5—a first chart related to the determination of the adhesive lines of the napkin illustrated in FIGS. 2 and 4.

By considering the parameters estimated for the $2^{nd}$ grade function which fits the model, we can conclude that "Shear" is mainly a function of the adhesive ratio (G) and the number of adhesive lines (L) in smaller grade, and therefore the length of the adhesive lines 4,6 can be adjusted to any level recommended by the process or product conditions. We have the function below as a model:

$$Y=b_0+b_1.G+b_2.(L)^2$$

wherein "Y" represents the value of "Shear", "L" is the number of adhesive lines and "G" is the adhesive ratio. The values of "b" are the determined coefficients and they are respectively: (−13.73); 0.66 and 0.004.

This function has also a "dominating point" as a solution. Within the studied interval it presents as solution the value of "Shear" as being 3.18 for an adhesive ratio of 23.6 g/m², for a 160 mm adhesive and with nineteen adhesive lines.

Figure 6:
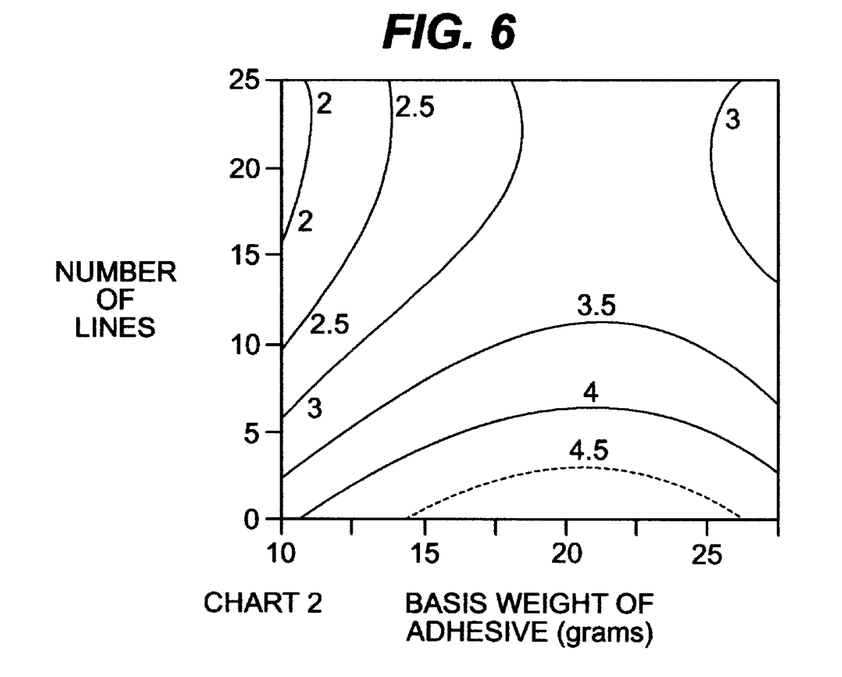
FIG. 6—a second chart related to the determination of the adhesive lines of the napkin illustrated in FIGS. 2 and 4.
Figure 7:
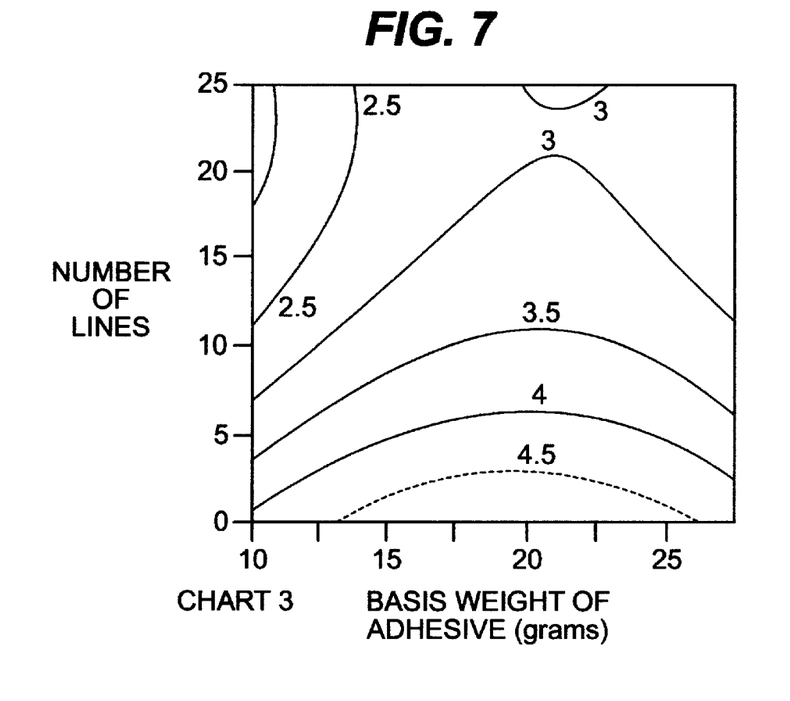
FIG. 7—a third chart related to the determination of the adhesive lines of the napkin illustrated in FIGS. 2 and 4.

Charts 2 and 3 represent level curves and allow us to analyze the influence of the two variables: the ratio and the number of the adhesive lines at the same time, keeping constant the length of the adhesive.

In chart 2, the value of "Shear" appears in terms of the adhesive ratio and the number of adhesive lines for a 180 mm adhesive.

We can observe that for a given adhesive ratio the "Shear" decreases very sharply with the increase of the number of adhesive lines tending to increase when the number of adhesive lines tends to infinite, that is, it approximates again to a single strap. For a fixed number of adhesive lines, an increase in the ratio also causes an increase in the value of "Shear".

In chart 3, wherein the value of "Shear" appears in terms of the adhesive ratio and the number of adhesive lines for a 190 mm adhesive, it can be seen that practically no change in the behavior is observed in relation to a 180 mm adhesive.

The same analysis can be carried out by fixating the adhesive ratio and observing how the "Shear" varies in terms of the length of the adhesive and the number of the adhesive lines.

Figure 8:
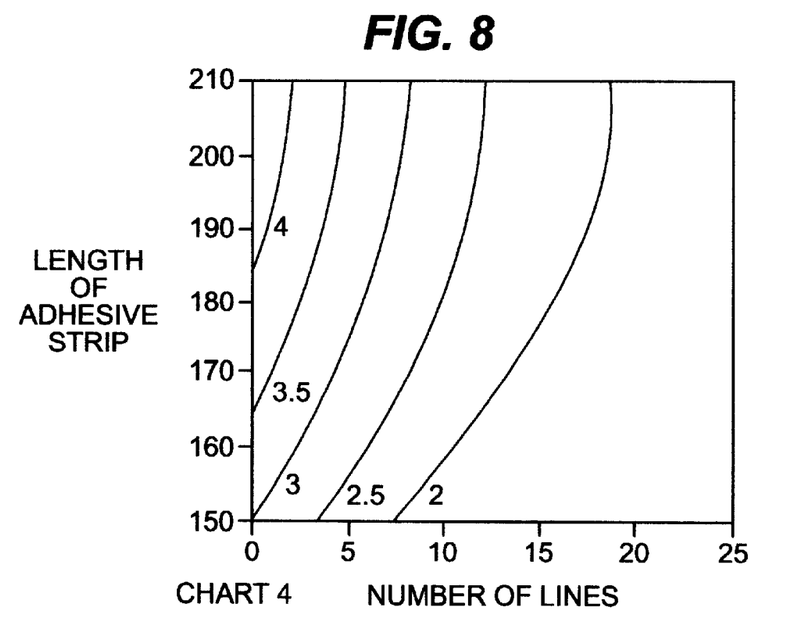
FIG. 8—a forth chart related to the determination of the adhesive lines of the napkin illustrated in FIGS. 2 and 4.

Chart 4 shows the value of "Shear" as a function of the length of the adhesive and the number of adhesive lines for a 10 g/m² ratio.

Figure 9:
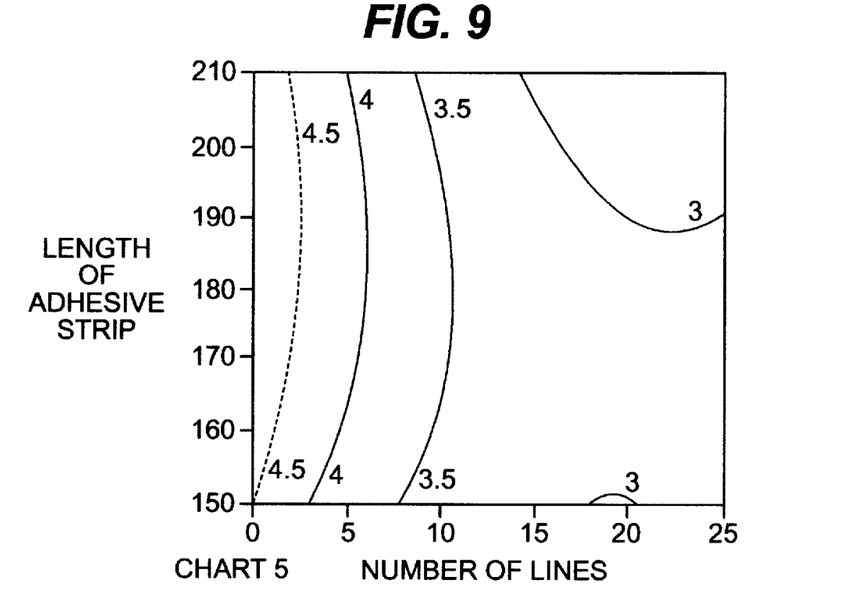
FIG. 9—a fifth chart related to the determination of the adhesive lines of the napkin illustrated in FIGS. 2 and 4.

There, the quasi-parallelism of the curves to the Y axis indicates a practically null effect of the length of the adhesive on the value of "Shear" and a strong influence of the number of adhesive lines, thus, when we change from a single strap to, for instance, eight adhesive lines, we will be strongly decreasing the "Shear" to any length of adhesive, whereas by maintaining a certain number of adhesive lines the "Shear" only will increase with an considerable increase in the length of the adhesive. This behavior is even more accentuated for greater ratios, as can be seen in chart 5, which shows the value of "Shear" as function of the length of the adhesive and the number of adhesive lines for a 20 g/m² ratio.

Figure 10:
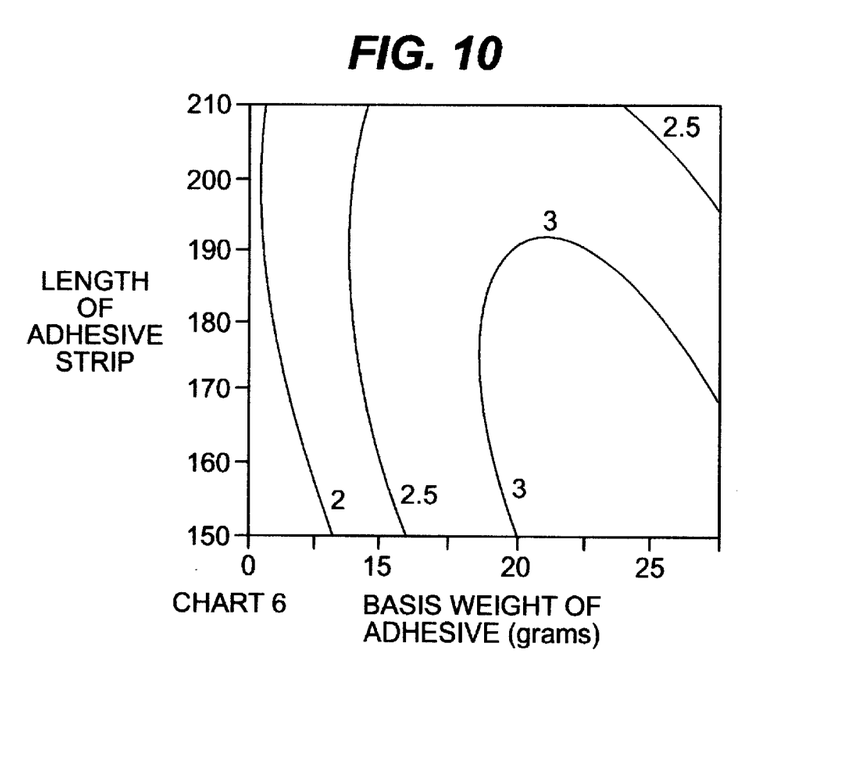
FIG. 10—a sixth chart related to the determination of the adhesive lines of the napkin illustrated in FIGS. 2 and 4.
Figure 11:
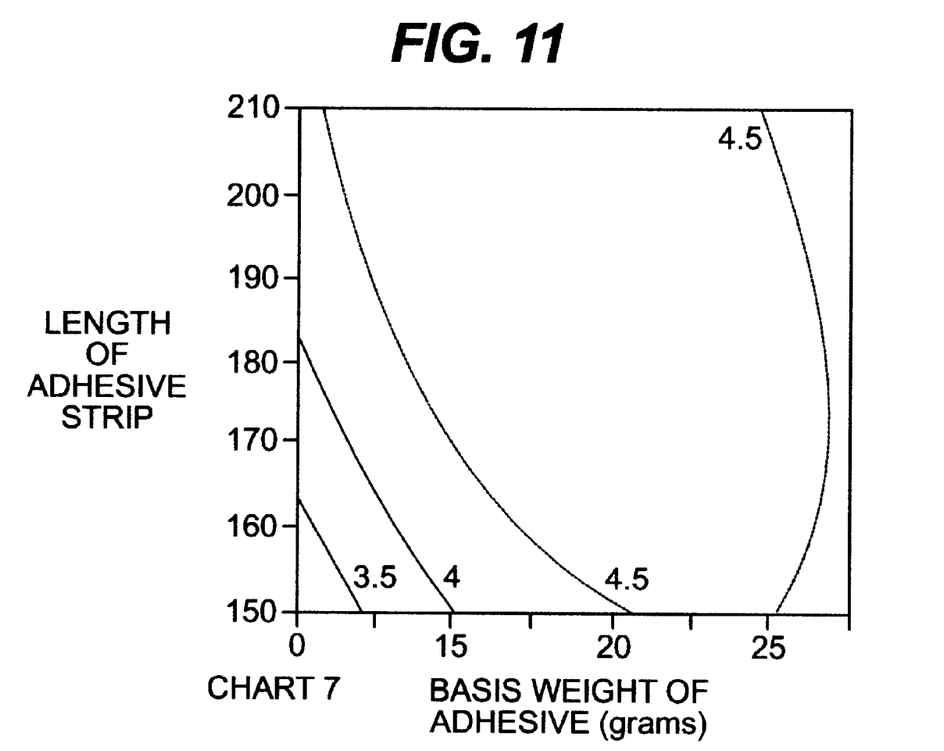
FIG. 11—a seventh chart related to the determination of the adhesive lines of the napkin illustrated in FIGS. 2 and 4.

Finally, by maintaining constant the number of adhesive lines, we can analyze how the "Shear" varies in terms of the ratio and length of the adhesive, according to charts 6 and 7. Chart 6 shows the value of "Shear" as function of the length of the adhesive and the ratio of adhesive for a number of adhesive lines wherein L=20. We observe from chart 6 that there is a directly proportional relationship between the adhesive ratio and the value of "Shear" in a certain interval, that is, it would be useless to increase indefinitely the adhesive ratio because this increase is not followed by the same response to "Shear".

The same is applicable to a single adhesive strap, according to chart 7, which presents the value of "Shear" as a function of the length of the adhesive and the adhesive ratio for a single adhesive strap (L=0).

If we establish a 180 mm length, which is the specification of the product, we would have:

Value of "Shear" given as solution by RSM: 3.18 kgf (1 Kgf=9.8 N)

Adhesive ratio: which can range from 8 to 25 g/m²

Number of adhesive lines: which can range from 5 to 25

After having described an example of a preferred realization, it must be understood that the scope of the present invention encompasses other possible variations, such as the application, to the lining sheet of the napkin 1,1', of an adhesive element formed by adhesive lines in which might comprise continuous or discontinuous adhesive lines 4,6 applied substantially transverse, perpendicular and/or inclined to one another can present directions substantially transversal, perpendicular and/or inclined to the longitudinal length of the frame 3,3', thus characterizing different standards such as losanges, trapezes, squares or any other standard known by those skilled in the art.

What is claimed is:

1. An intimate napkin for use with an undergarment, comprising:

a substantially planar and elongated frame comprising a first face having a liquid pervious material layer, and a second face, opposite to the first face, having a liquid impervious material layer;

an absorbing core inserted in the frame between the liquid pervious material layer and the liquid impervious material layer, the liquid impervious material layer comprising a first inner surface faced to the core, and a second outer surface, opposite to the first surface, faced outwardly, which constitutes an outer face of the napkin; and an adhesive layer applied to the second outer surface of the napkin, wherein the adhesive layer is comprised of at least eight lines of adhesive substantially spaced apart and arranged substantially longitudinally, said lines of adhesive extending substantially along an entire longitudinal dimension of the frame, the adhesive ratio ranges from 8 to 25 g/m², and the adhesive layer has a shear value of at least 2.0 Kgf.

2. The napkin, as claimed in claim 1, wherein the adhesive layer comprises from five to twenty-five lines of adhesive substantially parallel to one another, arranged substantially longitudinally.

3. The napkin, as claimed in claim 1, wherein the adhesive layer comprises from eight to twenty lines of adhesive substantially parallel to one another, arranged substantially longitudinally.

4. The napkin, as claimed in claim 1, wherein the adhesive layer comprises twelve lines of adhesive substantially parallel to one another, arranged substantially longitudinally.

5. The napkin, as claimed in claim 1, wherein the napkin further comprises two tabs projecting substantially outwardly from the frame, each of the tabs has at least two adhesive lines substantially spaced apart.

6. The napkin, as claimed in claim 5, wherein the adhesive lines on the tabs are substantially parallel to one another and are arranged substantially longitudinally on the tabs.

7. The napkin, as claimed in claim 1, wherein the adhesive layer has a shear value of about 3.18 Kgf.

8. The napkin, as claimed in claim 5, wherein the adhesive layer has a shear value of about 3.18 Kgf.

9. The napkin, as claimed in claim 1, wherein the adhesive lines have a width from 0.5 millimeters to 2.0 millimeters.

10. The napkin, as claimed in claim 1, wherein the adhesive lines have a width from 1.0 millimeters from 1.8 millimeters.

11. The napkin, as claimed in claim 1, wherein the adhesive lines have a width of about 1.2 millimeters.

12. The napkin, as claimed in claim 1, wherein a region intermediate adjacent lines of adhesive has a width from 0.8 millimeters to 2.5 millimeters.

13. The napkin, as claimed in claim 12 wherein the region has a width from 1.0 milimeters to 1.8 milimeters.

14. The napkin, as claimed in claim 12 wherein the region has a width of about 1.2 milimeters.

15. The napkin, as claimed in claim 5, wherein the adhesive lines have a width from 0.5 millimeters to 2.0 millimeters.

16. The napkin, as claimed in claim 5, wherein the adhesive lines have a width from 1.0 millimeters from 1.8 millimeters.

17. The napkin, as claimed in claim 5, wherein the adhesive lines have a width of about 1.2 millimeters.

18. The napkin, as claimed in claim 5, wherein a region intermediate adjacent of adhesive line has a width from 0.8 millimeters to 2.5 millimeters.

19. The napkin, as claimed in claim 18 wherein the region has a width from 1.0 millimeters to 1.8 millimeters.

20. The napkin, as claimed in claim 18 wherein the region has a width of about 1.2 millimeters.

21. The napkin, as claimed in claim 5, wherein the adhesive lines have a width from 0.5 millimeters to 1.5 millimeters.

22. The napkin, as claimed in claim 5, wherein the adhesive lines have a width from 0.8 millimeters to 1.2 millimeters.

23. The napkin, as claimed in claim 5, wherein the adhesive lines have a width of about 1.0 millimeters.

24. The napkin, as claimed in claim 5, wherein a region intermediate adjacent of adhesive line has a width from 0.8 millimeters to 2.0 millimeters.

25. The napkin, as claimed in claim 5, wherein the region has a width from 1.0 millimeters to 1.8 millimeters.

26. The napkin, as claimed in claim 5, wherein the region has a width of about 1.2 millimeters.

* * * * *